United States Patent [19]

Shin

[11] Patent Number: 5,117,061
[45] Date of Patent: May 26, 1992

[54] PROCESS OF PREPARING SUBSTITUTED ANILINES

[75] Inventor: Kju H. Shin, Baton Rouge, La.

[73] Assignee: Ethyl Corporation, Richmond, Va.

[21] Appl. No.: 861,823

[22] Filed: May 12, 1986

Related U.S. Application Data

[63] Continuation-in-part of Ser. No. 719,532, Apr. 3, 1985, abandoned, which is a continuation-in-part of Ser. No. 448,247, Dec. 9, 1982, abandoned, and a continuation-in-part of Ser. No. 448,404, Dec. 9, 1982, abandoned.

[51] Int. Cl.$^5$ .................. C07C 209/24; C07C 209/26
[52] U.S. Cl. ..................... 564/384; 564/305; 564/321; 564/330; 564/331; 564/333; 564/389; 564/341; 564/392
[58] Field of Search ............... 564/330, 331, 333, 384, 564/389, 391, 392, 305, 321

[56] References Cited

U.S. PATENT DOCUMENTS

| | | | |
|---|---|---|---|
| 1,999,069 | 4/1935 | Suter | 564/384 |
| 2,900,216 | 8/1959 | Schwechten et al. | 564/389 X |
| 2,962,531 | 11/1960 | Coffield | 564/389 |
| 3,068,298 | 12/1962 | Huffman | 564/384 X |
| 3,173,952 | 3/1965 | Farrar | 564/389 |
| 3,272,869 | 9/1966 | O'Shea | 564/384 X |
| 3,375,264 | 3/1968 | Sayigh et al. | 564/384 X |
| 3,383,415 | 5/1968 | Carabateas | 564/384 |
| 3,406,024 | 10/1968 | Richter et al. | 564/389 X |
| 3,629,250 | 12/1971 | Mutsch | 564/384 X |
| 3,857,890 | 12/1974 | Recchia et al. | 564/384 X |
| 3,969,409 | 7/1976 | Miyano et al. | 564/384 X |
| 4,157,343 | 6/1979 | Shoffner | 564/384 |
| 4,372,956 | 2/1983 | Ott | 564/389 X |

OTHER PUBLICATIONS

Miocque et al., (I), (II), and (III), Chemical Abstracts, vol. 73, p. 338, sections 130710z 130711a, and 130712b (1970).
Le Floch et al., Chemical Abstracts, vol. 93, p. 874, section 93:46084d (1980).
Miocque et al. (IIIa), Bull. Soc. Chim. Fr., 1970, pp. 1901–1907, esp. 1901 and 1904.
Saunders et al., Polyurethanes Chemistry and Technology, Pt. I. Chemistry, Interscience Publishers, New York, 1962, pp. 63–65.
Nissen et al., Aromatic Diamines as Chain Extenders in RIM Urethane Elastomers, pp. 71–78 (1982).
Badendorf et al., "Ann", vol. 592, pp. 26–37 (1955).
Translation "Houben–Weyl Methoden der Organischen Chemie", 4th Ed., vol. 14/2 pp. 293–295 (1963).

*Primary Examiner*—Richard L. Raymond
*Attorney, Agent, or Firm*—Patricia J. Hogan

[57] ABSTRACT

Novel anilines of the 2,6-dialkyl-4-dialkylaminomethylaniline type are prepared by reacting a secondary amine and an aldehyde with a primary aniline reactant having a free para position and substituents in both ortho positions in the presence of an acid catalyst, the amounts of amine and acid employed being at least equimolar with respect to the amount of aldehyde, and the reaction being conducted by adding the primary aniline reactant to a preformed mixture of the secondary amine, aldehyde, and acid.

13 Claims, No Drawings

PROCESS OF PREPARING SUBSTITUTED ANILINES

CROSS-REFERENCE TO RELATED APPLICATIONS

This application is a continuation-in-part of copending application Ser. No. 719,532, filed April 3, 1985, now abandoned, which in turn is a continuation-in-part of U.S. applications Ser. No. 448,247 and Ser. No. 448,404, both filed Dec. 9, 1982, and both now abandoned.

FIELD OF THE INVENTION

This invention relates to substituted anilines of the 2,6-dialkyl-4-dialkylaminomethylaniline type and to processes for preparing them.

BACKGROUND

It is known that alkylidene bisarylamines, especially substituted methylene bisanilines, are useful as curing agents and chain extenders for polyurethanes and that asymmetrical bisanilines are frequently preferable to symmetrical bisanilines in these applications. However, processes for preparing asymmetrical methylene bisanilines from known reactants are apt to be inefficient because of their resulting in the co-formation of significant amounts of symmetrical methylene bisanilines as contaminants. Thus, there is a need for the provision of compounds that would be suitable for use in synthesizing asymmetrical methylene bisanilines uncontaminated with substantial amounts of symmetrical byproducts.

As disclosed in Miocque et al., *Chemical Abstracts*, Vol. 73, p. 338, sections 130710z, 130711a, and 130712b (1970), it is known that a secondary or tertiary aniline or toluidine can be reacted with formaldehyde and a secondary amine to form a Mannich base. However, it is also known that previous attempts to prepare Mannich bases from primary anilines have been unsuccessful. As taught in Miocque et al., *Bulletin de la Societe Chimique de France*, 1970, pp. 1901-1907, it was previously believed to be only theoretically possible to prepare a Mannich base of a primary aniline directly from the primary aniline rather than by an indirect route, such as by the initial formation of a Mannich base of an N-benzylaniline, followed by cleavage with sodium in liquid ammonia.

SUMMARY OF THE INVENTION

An object of this invention is to provide novel substituted anilines.

Another object is to provide such compounds which are useful as chemical intermediates.

Still another object is to provide such compounds which are useful in the production of high yields of methylene bisanilines.

A further object is to provide a novel Mannich reaction for preparing such compounds.

Another object is to provide such a reaction which permits the formation of a Mannich base from a primary aniline.

These and other objects are attained by adding a primary aniline reactant having a free para position and substituents in both ortho positions to a mixture of one molar proportion of an aldehyde corresponding to the formula RCHO, at least one molar proportion of a secondary amine corresponding to the formula HNR'R", and at least one molar proportion of an acid catalyst and heating the resultant reaction mixture at a temperature in the range of about 30-150° C. so as to form a primary aniline product having a —CHR—NR'R" group para to the primary amino group, the positions ortho to the primary amino groups in the aniline reactant and product, as well as any other substituted ring positions, being occupied by substituents independently selected from halogenated and unhalogenated alkyl, cycloalkyl, and aryl groups; R being hydrogen, alkyl, cycloalkyl, or aryl, and R' and R" being independently selected from alkyl, hydroxyalkyl, cycloalkyl, hydroxycycloalkyl, and aryl.

DETAILED DESCRIPTION

Primary anilines utilizable as reactants in the practice of the invention can be any primary anilines having a free para position and having the ortho positions, as well as any other substituted ring positions, occupied by substituents independently selected from halogenated and unhalogenated alkyl, cycloalkyl, and aryl groups. However, they are usually such compounds wherein the substituents contain 1-20 carbons. The preferred anilines are those in which any alkyl substituents contain 1-6 carbons, any cycloalkyl substituents contain 5-8 carbons, any aryl substituents contain 6-12 carbons, and any halogenated substituents are chlorinated or brominated substituents; and it is also generally preferred for the anilines to be 2,6-disubstituted anilines having no additional substituents.

Exemplary of the primary anilines that can be employed as reactants are the 2,6-dimethyl-, diethyl-, diisopropyl-, di-t-butyl-, dipentyl-, dihexyl-, dicyclopentyl-, and di-alpha-methylbenzylanilines etc.; the 2-ethyl-, 2-isopropyl-, 2-t-butyl-, 2-secdodecyl-, 2-sec-eicosyl-, 2-cyclohexyl-, 2-cyclooctyl-, 2-phenyl-, 2-benzyl-, and 2-trichloromethyl-6-methylanilines, etc.; the 2-(2,2,2-trichloroethyl)-, 2-(trichloromethylbutyl)-, and 2-tribromomethyl-6-isopropylanilines, etc.; the corresponding 2-substituted 6-t-butylanilines; 2,3,6-trimethylaniline; 2,3,5,6-tetramethylaniline; 2,3-dimethyl-6-trichloromethylaniline; 2-sec-eicosyl-3,6-dimethylaniline, etc.

The amount of primary aniline reactant employed is typically a substantially equimolar amount, based on the amount of aldehyde used, although lesser amounts can also be beneficially employed. It is generally preferred not to use an amount much in excess of the equimolar amount because of the by-product formation that is apt to be encouraged by an excess of the aniline.

As indicated above, secondary amines that can be used in the process include most secondary amines However, they are generally amines wherein R' and R" of the HNR'R" formula are groups containing 1-20 carbons; and, for reasons of cost and availability, as well as performance, the preferred secondary amines are dialkylamines and hydroxyalkylamines, most preferably such amines wherein the alkyl groups contain 1-6 carbons.

In a particularly preferred embodiment of the invention, the amine is one that has a boiling point not higher than about 120° C., i.e., a dialkylamine wherein the alxyl groups contain 1-3 carbons. The products formed from these amines are believed to be particularly valuable because of increased reactivity.

Exemplary of utilizable secondary amines are the dimethyl-, diethyl-, diisopropyl-, methylethyl-, di-2-hydroxyethyl-, di2-hydroxypropyl-, di-2-hydroxybutyl- , ethyl-2-hydroxyethyl-and diphenylamines, as well as other such amines when R' and R" are independently selected from methyl, ethyl, isopropyl, isobutyl, triacontyl, 2-hydroxyethyl, 2-hydroxypropyl, 2hydroxybutyl, cyclopentyl, cyclohexyl, cyclooctyl, 4-hydroxycyclohexyl, phenyl, o-tolyl, benzyl, alpha-methylbenzyl, etc.

In the practice of the invention, the secondary amine may be employed per se or in the form of an acid salt, e.g., a salt of sulfuric, hydrochloric, nitric, acetic, propionic, benzoic, etc., acid. The amount of secondary amine used is at least equimolar, based on the amount of aldehyde employed, and it is generally in the range of about 1–5 mols, preferably about 1–2 mols, per mol of aldehyde.

The aldehyde reactant may be any aldehyde corresponding to the above RCHO formula, such as formaldehyde, acetaldehyde, propionaldehyde, butyraldehyde, isobutyraldehyde, 2-ethylhexanal, dodecanal, benzaldehyde, 4-t-butyraldehyde, 2-phenylacetaldehyde, cyclohexaldehyde, cyclooctylaldehyde, 2-cyclohexylacetaldehyde, etc. However, it is generally an aldehyde containing 1–20 carbons and is preferably formaldehyde, which may be employed per se or as a formaldehyde precursor, such as paraformaldehyde or 1,3,5-trioxane.

Acids that can be used to catalyze the reaction may be organic or inorganic acids, such as hydrochloric, hydrobromic, trifluoroacetic, trichloroacetic, acetic, formic, benzenesulfonic, p-toluenesulfonic, etc.; and they may be incorporated as separate compounds or as the secondary amine salts mentioned above. Acetic acid is generally preferred. The amount of acid employed must be at least an equimolar amount, based on the amount of aldehyde used, and should be at least equimolar with respect to the amount of secondary amine utilized. There does not appear to be any maximum to the amount of acid that may be employed, although a large excess is apt to be undesirable for economic reasons.

As mentioned above, the process of the invention is conducted by adding the primary aniline reactant to a preformed mixture of the aldehyde, secondary amine, and acid and accomplishing the reaction at a temperature of about 30–150° C. Any such technique is utilizable, but it is normally preferred to heat the preformed mixture before adding the primary aniline reactant and then to add that reactant gradually. In one embodiment of the invention, the reaction is effected by combining the secondary amine and aldehyde in a suitable solvent, adding the acid catalyst, and then gradually adding the primary aniline reactant while heating the secondary amine, aldehyde, and acid. Solvents suitable for use in this reaction include water and/or alcohols, such as methanol, ethanol, isopropanol, isobutanol, isoamyl alcohol, 2-methoxyethanol, etc.; water-miscible aprotic solvents, such as dimethylsulfoxide, dimethylformamide, methylpyrrolidone, etc., and mixtures thereof with water; mixtures of water with other solvents, such as heptane, cycloheptane, cyclohexane, isooctane, toluene, xylene, methylene chloride, ethylene dichloride, tetrahydrofuran, glyme, dioxane, diglyme, triglyme, etc., the preferred solvent being methanol. It is generally preferred to conduct the reaction at a moderate temperature, e.g., reflux temperatures in the range of 30–150° C., more preferably about 30–130° C., because of the possibility of increased by-product formation as the temperature is increased.

Exemplary of the primary aniline products, i.e., Mannich bases, that can be prepared in the practice of the invention are the 2,6-dimethyl-, 2,6-diethyl-, 2,6-diisopropyl-, 2,6-di-sec-butyl, 2,6-di-t-butyl-, 2,6-dioctyl-, 2,6-diphenyl-, 2,6-dicyclohexyl-, 2-ethyl-6-isopropyl-, 2-methyl-6-sec-butyl; 2-methyl-6-t-butyl-, 2-amyl-6-methyl-, 2-trichloromethyl6-isobutyl-, 2-tribromomethyl-6-t-butyl-, 2-ethyl-6-benzyl-, 2-cyclopentyl-6-methyl-, and 2-cyclopentyl-6-sec-butyl-4-dimethylaminomethyl anilines) the corresponding 2,6-disubstituted-4-diethanolaminomethyl-, 4-diisoproanolaminomethyl-, 4-dimethylaminobenzyl-, 4-diethanolaminobenzyl-, 4-dicyclopentylaminobenzyl-, 4dihexylaminomethyl-, 4-methyl-t-butylaminomethyl-, 4-isopropyl-ethylaminobenzyl-, 4-ethylethanolaminomethyl-, 4-[1-(dimethylamino)propyl]-, and 4-[1-diethanolamino)butyl]anilines; 2,3,6-triisopropyl- and 2,3,5,6-tetramethyl-4-dimethylaminomethyla etc.

These compounds are particularly valuable as intermediates for the preparation of bisanilines, such as asymmetrical methylene bisanilines which are useful as curing agents and chain extenders for polyurethanes and bisanilines that are useful as crosslinking agents for epoxy resins. When such bisanilines are desired, they may be prepared by alkylating an arylamine having at least one free ortho or para position with a product of the present process, generally a product having ring substituents different from those on the aromatic ring of the arylamine and generally under substantially anhydrous conditions in the presence of an acid catalyst, so as to form an alkylidene bisarylamine.

The invention is particularly advantageous in providing precursors for use in such bisaniline syntheses, but it is also generally useful in providing Mannich bases having other applications, e.g., use as antioxidants, agricultural chemicals, intermediates for physiologically-active materials, etc.

The following examples are given to illustrate the invention and are not intended as a limitation thereof.

EXAMPLE I

A suitable reaction vessel containing 78 mmols of acetic acid at ice-water bath temperature was slowly charged with 35 mmols of 40% aqueous dimethylamine and then with 33 mmols of 37% aqueous formaldehyde. The mixture was cooled to 5° C., and 33 mmols of 2,6-diisopropylaniline were added in three portions over a period of five minutes. Then the reaction mixture was maintained at room temperature for about 20.5 hours, during which two additions of 10 ml of methanol were made. When it was observed that only limited reaction had occurred, the temperature was raised to 72° C. and reaction was conducted at that temperature for seven hours. The reaction mixture was then cooled and worked up to provide 4.2 g of a crude product which was determined by gas chromatography (GC) to be 92% pure 2,6-diisopropyl-4-dimethylaminomethylaniline. The identity of the compound was confirmed by mass spectroscopy (MS), nuclear magnetic resonance (NMR), and infrared (IR) analyses.

EXAMPLE II

A suitable reaction vessel containing 0.55 mol of 40% aqueous dimethylamine at ice-water bath temperature was slowly charged with 1.2 mols of acetic acid, followed sequentially by 100 ml of methanol and 0.55 mol of 37% aqueous formaldehyde. Then the ice-water bath was removed, and 0.5 mol of 2,6-dimethylaniline was slowly added as the reaction mixture warmed to room temperature. The mixture was then heated to 81° C. over a period of about one hour, maintained at about 81° C. for an additional 2.5 hours, cooled, and worked up to provide 12.5 g of a crude product. GC analysis showed 70.6 area % of this product to be a Mannich base which was identified as 2,6-dimethyl-4-dimethylaminomethylaniline by MS and NMR analyses.

EXAMPLE III

A mixture of 0.80 mol of dimethylamine hydrochloride, 0.86 mol of acetic acid, and 0.70 mol of 37% aqueous formaldehyde was heated to 70° C., with 0.67 mol of 2,6-diisopropylaniline being added dropwise over a period of 80 minutes after the temperature reached 45° C. After a total heating time of two hours, the reaction mixture was allowed to cool and was then worked up. GC analysis of the reaction mixture showed 82.6 area % of 2,6-diisopropyl-4-dimethylaminomethylaniline.

EXAMPLE IV

A mixture of 0.40 mol of dimethylamine, 0.35 mol of 37% aqueous formaldehyde, and 0.43 mol of acetic acid was warmed to a bath temperature of 45° C., and 0.33 mol of 2-t-butyl-6-methylaniline was added over a period of about 1.5 hours as the pot temperature was increased to and maintained at about 72° C. Cooking was continued to give a total reaction time of two hours. GC analysis did not detect any unreacted aniline and showed the yield of 2-t-butyl-6-methyl-4-dimethylaminomethylaniline to be 75.4 area and the yield of 4,4'-methylene-bis(2-t-butyl-6-methylaniline) by-product to be 20.2 area %.

The reaction mixture was diluted with 150 ml of toluene, adjusted to a pH of about 7, and vigorously stirred, after which the toluene layer, which contained substantially all of the bisaniline by-product, was removed. Subsequently the remaining reaction mixture was adjusted to a pH of about 12 to free the Mannich base product from its salt form, toluene was added to extract the Mannich base, and the toluene phase was subjected to distillation to provide 2-t-butyl-6-methyl-4-dimethylaminomethylaniline containing only small amounts of impurities.

EXAMPLE V

A mixture of 0.7 mol of dimethylamine hydrochloride, 0.7 mol of acetic acid, and about 0.7 mol of 37% aqueous formaldehyde was heated to 62° C. over a period of 0.5 hour with stirring. Then about 0.7 mol of 2,6-diethylaniline was added over a period of one hour at 70° C., and the reaction was continued for a further 0.5 hour at 70° C. At this point, the 2,6-diethylaniline was completely converted, and GC analysis of the reaction mixture showed a 2,6-diethyl-4-dimethylaminomethylaniline to 2,2',6,6'-tetraethyl-4,4'-methylene bisaniline area % ratio of 2.47/1.

EXAMPLE VI

A suitable reaction vessel containing 0.55 mol of 40% aqueous dimethylamine, 1.17 mols of acetic acid, 100 ml of methanol, and 0.55 mol of 37% aqueous formaldehyde was allowed to warm to room temperature while adding 0.5 mol of 2,6-dimethylaniline. The reaction mixture was then heated, maintained at 67-81° C. for about three hours, cooled, and worked up to provide a crude product which was determined by GC analysis to contain 2,2',6,6'tetramethyl-4,4'-methylenebisaniline and 2,6-dimethyl-4-dimethylaminomethylaniline in an area % ratio of 1.7/1.0, as well as a small amount of 2,6-dimethyl-4-methoxymethylaniline.

What is claimed is:

1. A process which comprises adding a primary aniline reactant having a free para position and substituents in both ortho positions to a mixture of one molar proportion of an aldehyde corresponding to the formula RCHO, at least one molar proportion of a secondary amine corresponding to the formula HNR'R", and at least one molar proportion of an acid catalyst and heating the resultant reaction mixture at a temperature in the range of about 30–150° C. so as to form a primary aniline product having a —CHR—NR'R" group para to the primary amino group, the positions ortho to the primary amino groups in the aniline reactant and product, as well as any other substituted ring positions, being occupied by substituents independently selected from halogenated and unhalogenated alkyl, cycloalkyl, and aryl groups; R being hydrogen, alkyl, cycloalkyl, or aryl, and R' and R" being independently selected from alkyl, hydroxyalkyl, cycloalkyl, hydroxycycloalkyl, and aryl.

2. The process of claim 1 wherein the primary aniline reactant is a 2,6-disubstituted aniline.

3. The process of claim 2 wherein the substituents on the ring of the primary aniline are alkyl groups containing 1–6 carbons.

4. The process of claim 1 wherein the aldehyde is formaldehyde.

5. The process of claim 1 wherein the secondary amine is a dialkylamine in which the alkyl groups contain 1–6 carbons.

6. The process of claim 5 wherein the dialkylamine is dimethylamine.

7. The process of claim 1 wherein a dialkylamine and formaldehyde are reacted with a 2,6-dialkylaniline, the alkyl groups in the dialkylamine and aniline being alkyl groups containing 1–6 carbons.

8. The process of claim 1 wherein the catalyst is acetic acid.

9. The process of claim 1 wherein the reaction is conducted in an alcohol solvent.

10. The process of claim 1 wherein the reaction is conducted at reflux temperature.

11. The process of claim 1 wherein the reaction is conducted at a temperature in the range of about 30–130° C.

12. The process of claim 1 wherein the reactants are combined by gradually adding the primary aniline reactant to a preheated mixture of the secondary amine, aldehyde, and acid.

13. The process of claim 1 wherein the primary aniline product is recovered by (a) extracting any formed alkylidene bisaniline in an organic solvent phase, (b) raising the pH of the remaining product to free the primary aniline product from its salt form, and (c) extracting the free primary aniline product in an organic solvent phase.

* * * * *